US008449590B2

(12) United States Patent
Brader

(10) Patent No.: US 8,449,590 B2
(45) Date of Patent: May 28, 2013

(54) APPARATUS AND METHOD FOR PREVENTING BRAIN DAMAGE DURING CARDIAC ARREST, CPR, OR SEVERE SHOCK

(76) Inventor: Eric William Brader, Wexford, PA (US)

( * ) Notice: Subject to any disclaimer, the term of this patent is extended or adjusted under 35 U.S.C. 154(b) by 1002 days.

(21) Appl. No.: 12/433,640

(22) Filed: Apr. 30, 2009

(65) Prior Publication Data

US 2009/0276018 A1  Nov. 5, 2009

Related U.S. Application Data

(60) Provisional application No. 61/049,203, filed on Apr. 30, 2008.

(51) Int. Cl.
*A61F 7/00* (2006.01)

(52) U.S. Cl.
USPC ............................................ 607/110; 607/114

(58) Field of Classification Search
USPC ............ 607/96, 99, 104, 108–112, 114; 62/4, 62/530; 126/263.01–263.1; 190/900
See application file for complete search history.

(56) References Cited

U.S. PATENT DOCUMENTS

| 1,965,424 | A | * | 7/1934 | Mascolo | 128/203.26 |
| 4,265,286 | A | * | 5/1981 | Rapoport | 190/108 |
| 4,304,070 | A | | 12/1981 | Musacchia | |
| 4,920,963 | A | * | 5/1990 | Brader | 607/109 |
| 5,755,756 | A | | 5/1998 | Freedman, Jr. et al. | |
| 6,277,143 | B1 | * | 8/2001 | Klatz et al. | 607/104 |
| 6,289,889 | B1 | * | 9/2001 | Bell et al. | 126/263.07 |
| 7,040,115 | B1 | * | 5/2006 | Lopez et al. | 62/457.2 |

OTHER PUBLICATIONS

PCT International Preliminary Report on Patentability and Written Opinion of the International Searching Authority corresponding to PCT Application No. PCT/US20091042391 dated Nov. 11, 2010.

* cited by examiner

*Primary Examiner* — Linda Dvorak
*Assistant Examiner* — Adam Avigan
(74) *Attorney, Agent, or Firm* — Reed Smith LLP

(57) ABSTRACT

Apparatuses and methods for the cooling of the cranial and extracranial portions of a patient in need thereof. The apparatuses and methods of the present invention preferably employ a head cooling apparatus which includes a watertight shroud for the head and which needs no refrigeration. In certain preferred embodiments, the apparatuses of the present invention are collapsible and possess a reduced profile. In some presently preferred embodiments, the present invention includes a hammock that supports the head. In some embodiments, the present invention includes a shroud that lies behind the head with optional portions that may be drawn over the patient's neck and cranial area. The apparatuses and methods of the present invention also provide an improved mechanism for cooling the cranial and extracranial areas through the use of a novel distribution of endothermic solids (e.g. ammonium nitrate). The present invention provides a novel distribution of ammonium nitrate pellets that preferably includes multiple populations solid ammonium nitrate, preferably including small diameter (e.g., powdered) and larger diameter (e.g., 7 millimeter) ammonium nitrate to allow water initially to be cooled very quickly, thereby facilitating the rapid cooling of the cranial and extracranial areas, while at the same time producing extended hypothermia.

24 Claims, 13 Drawing Sheets

APPARATUS AND METHOD FOR PREVENTING BRAIN DAMAGE DURING CARDIAC ARREST, CPR, OR SEVERE SHOCK

CROSS-REFERENCE TO RELATED APPLICATIONS

This application claims priority to provisional patent application Ser. No. 61/049,203, filed Apr. 30, 2008.

BACKGROUND OF THE INVENTION

1. Field of the Invention

The present invention is a method of and apparatus for inhibiting tissue metabolism in the area of the brain and, more particularly, is a method and apparatus for inducing localized hypothermia and general hypothermia during the emergency treatment of cardiac arrest, severe shock, or systemic hypothermia in the treatment of other medical conditions such as stroke.

2. Description of the Background

Systemic hypothermia can dramatically postpone neurologic deterioration in hypoxic or anoxic tissues. Though initially thought to be due to reduced metabolism, since oxygen reserves are depleted early on in hypothermic cardiac arrest, hypothermic inhibition of triggering events during ischemia and reperfusion injury are now thought to be responsible for hypoxic injury. For example, accidental submersion in cold waters, and the commensurate systemic hypothermia thus produced, has consistently contributed to the neurologic survival of accident victims who otherwise would have sustained irreparable brain damage. Observation of this phenomenon led medical practitioners to induce systemic hypothermia in the course of various hypoxia and anoxia-producing surgical procedures in order to reduce both the systemic metabolism and the associated overall oxygen requirement of the patient.

Whereas systemic hypothermia may be induced with less difficulty in the hospital environment, emergency inducement of systemic hypothermia in a non-hospital setting can be difficult or impossible. As a result, induced systemic hypothermia forms no part of, for example, pre-hospital emergency cardiac care such as cardiopulmonary resuscitation (CPR), notwithstanding the beneficial metabolic inhibition which such hypothermia would provide. Similar emergency procedures in which hypothermia has not been induced to date include the pre-hospital emergency care administered to patients in severe shock or stroke. Cooling after cardiac arrest is being performed by paramedics via haphazard application of cold packs and infusion of cold intravenous fluids. Neither of these techniques have been studied or are necessarily relevant to patients suffering from cardiac arrest and would not be available to typical non-paramedic first responders.

Induced localized hypothermia has been used widely in the non- or pre-hospital treatment of numerous physiologic conditions. Cold packs of some sort are standard equipment in first aid kits, and are used to decrease peripheral blood flow and commensurate swelling in the event of contusion, insect bites or stings, nosebleeds, sprains, etc. Cold compresses to the head, of course, have long been a standard symptom-relieving measure for headaches and fever. In addition to these common treatments, however, three of the less well-known uses for topical cold applications are described in U.S. Pat. Nos. 2,438,643, 3,175,558 and 4,552,149.

U.S. Pat. No. 2,438,643 discloses a pack, for use in local refrigeration anesthesia, which contains a plurality of waterproof compartments which contain brine and an absorbent material, such as sawdust. The pack may be cooled in any suitable refrigerating device and then used as a topical cold pack. Because the pack must be refrigerated, its utility for inducing localized hypothermia is limited to those areas for which refrigeration is available.

U.S. Pat. No. 4,552,149 also discloses a coolant-containing, refrigerant-dependent cold pack which is, more specifically, a head coolant device. The device comprises a main body consisting of a cooling piece for covering the top of the head and a plurality of cooling pieces radially arranged around the main body, for covering the front, sides, and back of the head. This head cooling cap is designed to inhibit hair loss during the administration of a drug or chemotherapeutic agent for which hair loss is a known side effect. As with all cold packs which require refrigeration, the head coolant device is best suited to hospital and home application, and is not well suited for use in the types of pre-hospital emergency care for which refrigeration is commonly unavailable.

U.S. Pat. No. 3,175,558 discloses a thermal therapeutic pack, specifically designed for postpartum application to the female perineum, which contains the unreacted constituents of endothermic reaction. The unreacted constituents are separated by frangible barriers, time-release capsules, or both, and the separation is maintained until the cold pack is needed. At the time of use, the reactants are admixed by, for example, manually cracking the frangible barrier between them, thus commencing the endothermic reaction and reducing the overall temperature of the cold pack and its contents. The pack is positioned on the patient, as desired, to cool the area of application by the reverse conductive heating of the pack by the body.

In several prior art devices, the cooling of the fluid in the device is accomplished through an endothermic reaction between water and ammonium nitrate which are usually present as a single population of pellets. The amount of reactants and form of the reactants are generally chosen to produce a fluid that does not drop below freezing, where tissue may become frozen and subsequently suffer damage. While avoiding tissue damage, such conditions result in sub-optimal cooling of the patient, thus reducing the beneficial effects of cooling.

As noted above, those prior art patents possess deficiencies, such as requirements for electricity, that preclude their effective use in the emergency treatment of cardiac arrest or severe shock in the field. The inventions disclosed in U.S. Pat. Nos. 4,750,493 and 4,920,963 addressed and overcame those deficiencies. At the same time, the devices disclosed therein were relatively bulky with preferred dimensions of 2'×2'×2'. In combination with their preferred weight (25 pounds), the devices were limited in the areas where could be stored and deployed. Thus, there remains an unaddressed need in the medical community for portable devices with limited physical profiles that provide for inducing controlled hypothermia for cooling of the cranial and extracranial areas. In addition, there remains an unaddressed need for rapid and deep cooling of patients, while at the same time avoiding tissue damage from freezing.

SUMMARY OF THE INVENTION

The present invention encompasses apparatuses and methods for cooling the cranial and extracranial areas including the face, neck, scalp, and, optionally, the mandible, during emergency care of cardiac arrest, severe shock, or stroke. The apparatuses and methods of the present invention preferably employ a head cooling apparatus which includes a watertight shroud for the head and which needs no refrigeration.

In certain preferred embodiments, the apparatuses of the present invention are collapsible. When collapsed, the apparatuses would preferably possess a limited profile so that they could be stored in relatively small spaces or mounted to a wall. When wall mounted, the limited profile would reduce the likelihood that the devices would serve as an obstruction for passing foot traffic. As such, the present invention may be wall mounted in conjunction with an Automatic External Defibrillator (AED) device to facilitate simultaneous deployment.

The present invention preferably includes a mechanism for support and effective cooling of the patient's head within the devices of the present invention. IN some presently preferred embodiments, the present invention includes a hammock that supports the head. In some embodiments, the present invention includes a shroud that lies behind the head with optional portions that may be drawn over the patient's neck and cranial area. In some embodiments, the hammock and shroud may be combined into one element while in other embodiments they are separate components of the present invention.

The apparatuses and methods of the present invention also provide an improved mechanism for cooling the cranial and extracranial areas through the use of a novel distribution of endothermic solids. In the prior art, a single population of endothermic solid (described here with reference to the example of ammonium nitrate ($NH_4NO_3$)) pellets are used for cooling solutions by housing them in proximity to, but physically separated from, a volume of water. When a barrier between the two is disrupted, the water is allowed to react with the ammonium nitrate in an endothermic reaction, thus cooling the fluid. The present invention provides a novel distribution of ammonium nitrate pellets that preferably includes multiple populations solid ammonium nitrate to allow water initially to be cooled very quickly, thereby facilitating the rapid cooling of the cranial and extracranial areas, while at the same time producing extended hypothermia. The present invention further provides for a distribution of solid ammonium nitrate that produces cooling fluids which do not cause thermal damage. In some presently preferred embodiments, the distribution of pellets is chosen such that the water may be cooled slightly below freezing.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION OF THE INVENTION

Figure 1:
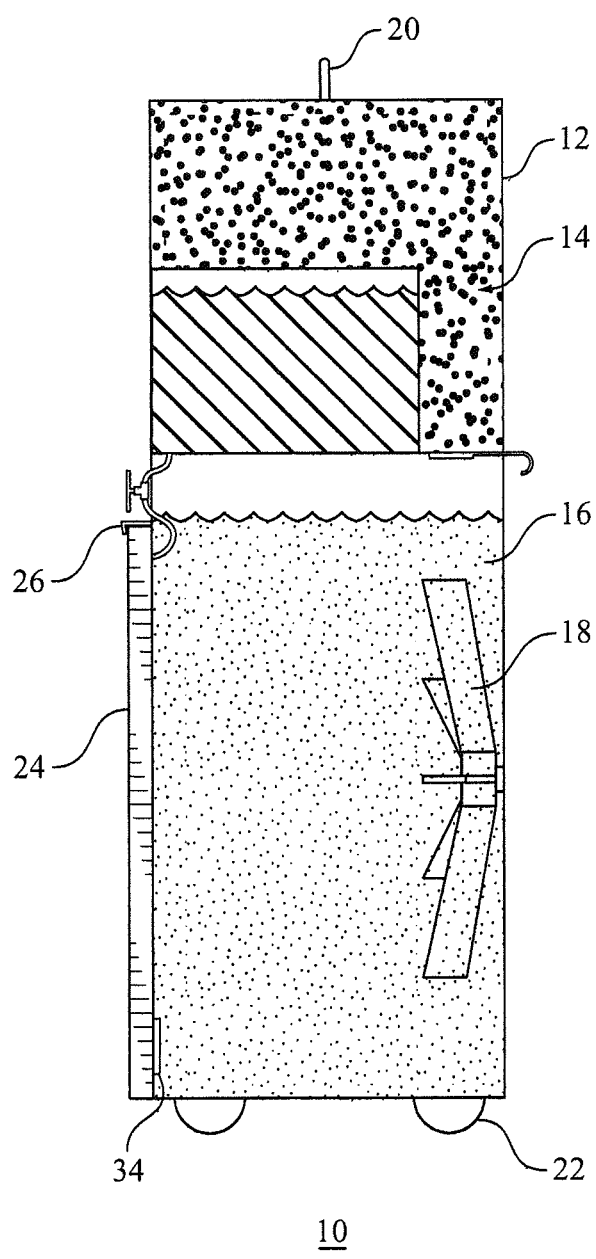
FIG. 1 is a cut-away view of a head cooling apparatus according to the present invention in a collapsed state.

It is to be understood that the figures and descriptions of the present invention have been simplified to illustrate elements that are relevant for a clear understanding of the invention, while eliminating, for purposes of clarity, other elements that may be well known. The detailed description will be provided herein below with reference to the attached drawings.

The present method for preventing or reducing brain damage during cardiac arrest, severe shock, or stroke comprises inducing localized hypothermia in the cranial and extracranial areas including the face, and optionally also including the mandible, in order to precipitate both extracranial vasoconstriction and intracranial cooling by conduction. This method of cooling the external area of the cranium without likewise cooling, for example, the torso and extremities, is moreover physiologically preferable to the more drastic induction of systemic hypothermia. Cranial cooling is preferred to systemic cooling for its obvious convenience in both in-hospital and pre-hospital patient care as well as being an immediate induction tool for application of mild systemic hypothermia upon return of circulation through re-equilibration. Since much ischemic/anoxic injury occurs and is triggered by reperfusion and restoration of tissue oxygenation, initiation of therapeutic mild systemic cooling immediately upon this event is possible by cooling during arrest or severe shock in anticipation of restoring normal perfusion albeit at a time which cannot be reliably predicted. Furthermore, post-arrest cooling generally requires intravenous access—a technique not performable by laymen, however, with CPR and utilization of AEDs, lay people and other first responders can now successfully resuscitate patients who would benefit from post-arrest hypothermia, but have no means to institute it. It is generally accepted that the earlier therapeutic hypothermia is instituted, the better the outcome for the patient.

Although any extracranial cooling is beneficial during respiratory or cardiac insufficiency, profound head cooling is preferred. Profound head cooling is particularly preferred during cardiac or respiratory arrest, for which resuscitation time is otherwise drastically limited. Frostbite avoidance and skin temperature monitoring may be carried out by means known in the art although, of course, frostbite is always preferable to neurologic loss. Profound cranial hypothermia is clinically feasible, due to the buffering of the cold venous return from the head by the warm venous return from the body. Apparently this buffering of cold venous return from the head is responsible for minimizing both unwanted afterdrop and undesirable myocardial and pulmonary cooling during treatment of the patient.

The present invention represents an improvement over U.S. Pat. No. 4,750,493 ("the '493 patent") and U.S. Pat. No. 4,920,963 ("the '963 patent"), which are hereby incorporated by reference in their entirety as if presented herein. The '963 patent discloses an apparatus for preventing brain damage during cardiac arrest, CPR, or severe shock. Due to its relatively large dimensions (2'×2'×2'), the locations where the device could be stored are limited. In addition, the crank shaft also represents a potential obstruction and trip hazard for individuals walking past the device. Furthermore, the apparatus disclosed in the '963 patent employed a single population of ammonium nitrate pellets which generated a smooth temperature descent to above-freezing levels to induce hypothermia in the cranial and extracranial regions.

The present invention improves upon that prior art in multiple regards. Firstly, the present invention provides a collapsible version of the devices disclosed in the '963 patent. The collapsible apparatuses of the present invention have a reduced profile so that they may be stored in a wide variety of locations without being a significant tripping or obstruction hazard. In one presently preferred embodiment, the collapsible apparatuses of the present invention may be mounted on a wall in a public place, much in the manner of AEDs that are commonly observed mounted on walls of public buildings. In certain presently preferred embodiments, the collapsed device will have a profile of approximately 7 inches, consistent with the commonly accepted profile of AEDs.

The head cooling apparatus of the present invention, shown in FIGS. 1-6, is a self-contained, portable system which enables application of cranial cooling regardless of location, whether in-hospital or at a remote location accessible only by emergency vehicle. The head cooling apparatus 10 in collapsed form is illustrated in FIG. 1. The apparatuses of the present invention 10 preferably include multiple compartments that house various operational aspects of the head cooling apparatus. For example, the present invention includes a compartment 14 that houses endothermic reaction pellets 12 with a separate reservoir 16 for the reactant water. The endothermic reaction pellets 14 are preferably housed above the water reservoir 16, though other geometric configurations (e.g., to the side of the water reservoir) may be employed. The water reservoir 16 is preferably of a capacity that it is able to contain both the water and the endothermic reaction pellets 14, though initially these two reactants are housed separately. The reservoir 16 once filled with reactants will be of sufficient verticality to hydrostatically force full deployment and maintain close approximation of the shroud to the patient and the hammock. The water reservoir 16 may include a rotational mixer 18 connected to a fold-away crank shaft that is shown in later figures.

A telescoping handle 20 may be included with the assembled head cooling apparatus 10 for easy transport. In some presently preferred embodiments, the invention will include a set of wheels or casters 22 placed at the bottom of the apparatus 10 along with a telescoping handle 20 to facilitate transportation of the device. In addition, the head cooling apparatuses of the present invention 10 may include hooks, loops, connectors, or other components that allow the apparatus to be connected to a wall, much in the manner of an AED.

Figure 2:
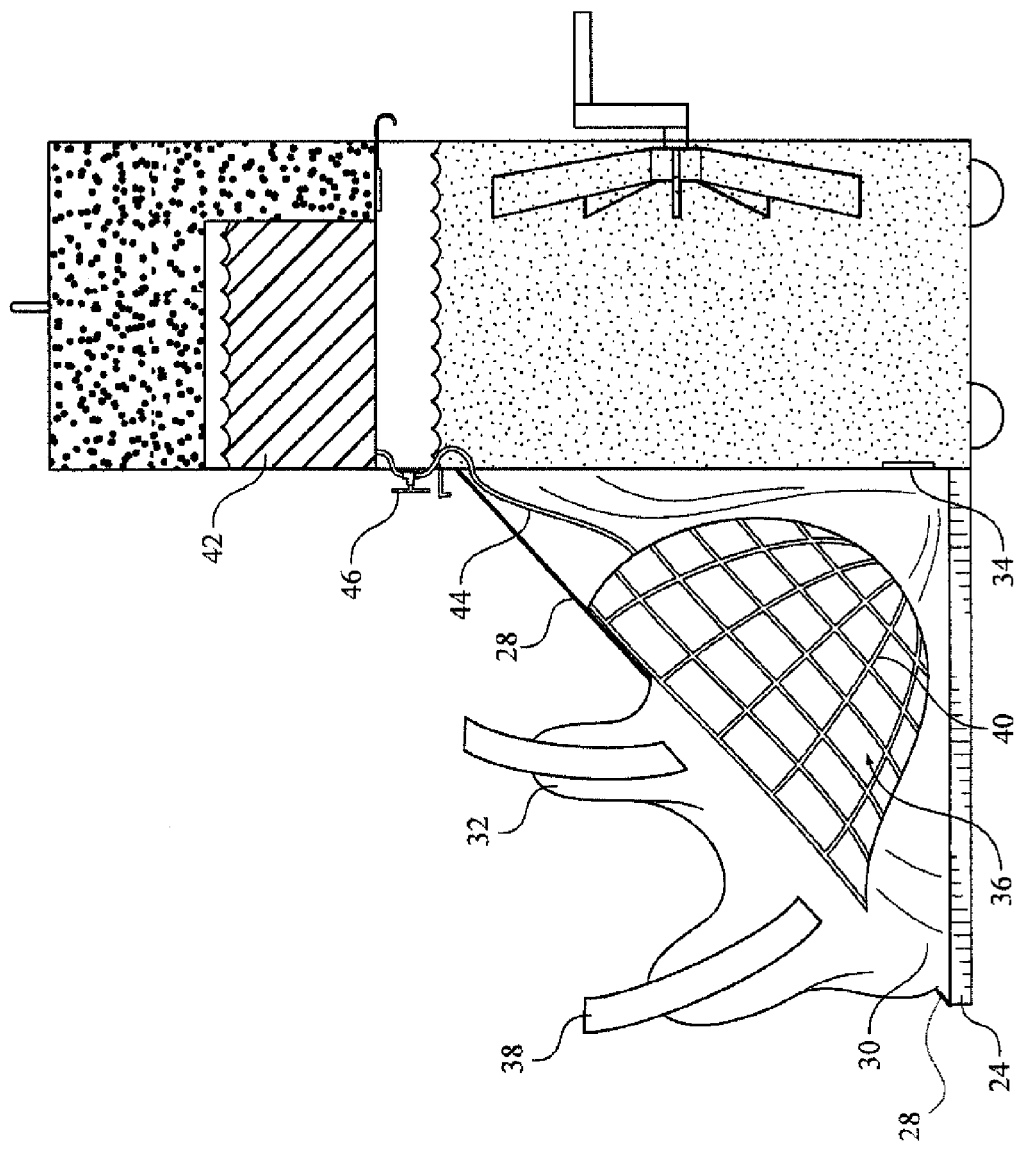
FIG. 2 is a cut-away view of a head cooling apparatus according to the present invention with the head hammock/shroud deployed.

As noted, the head cooling apparatuses of the present invention 10 preferably include a head shroud (not shown in FIG. 1) that may be housed behind a panel 24 when the present invention stored in a collapsed position, as shown in FIG. 1. The panel 24 may be held in its collapsed position through the use of latches, snaps, or other such components 26 well known to those of skill in the art. When the head cooling devices of the present invention 10 are deployed for use with a patient, the panel may be opened as shown in FIG. 2. The panel 24 is preferably attached to the main body of the head cooling device 10 via hinges at the bottom of the device. The panel 24 may be drawn downwards so that it rests substantially horizontal with the surface on which the heading cooling device of the present invention 10 is deployed. In some preferred embodiments, the panel 24 may lock in place to better support the patient's head. In some presently preferred embodiments, the panel 24 is fabricated from or includes within it an insulating material that reduces transfer of heat from the floor or ground to cooling fluid. At its distal end the panel 24 connects to a supporting cable or band 28. The other end of the supporting cable 28 is connected to the main body of the head cooling device 10. In presently preferred embodiments, the panel 10 is supported by two such supporting cables 28—one at the left-hand side of the panel and one at the right-hand side of the panel.

In one presently preferred embodiment, the supporting cables 28 support a watertight chamber 30 that includes a head shroud 32. The chamber 30 and head shroud 32 may be fabricated from a flexible material such as rubber or plastic. In one presently preferred embodiment, the watertight chamber 30 and head shroud 32 form a continuous watertight compartment that is separated from the water reservoir 16 by an internal panel 34. The watertight compartment 30 preferably includes loops that are disposed around the support cables 28. The head shroud 32 and hammock 36 are each preferably pre-shaped to form a pocket for the patient's head that is centrally located between the two support cables 28. In this embodiment, the shroud 32 may be physically joined to the hammock 36 as shown in FIG. 2-6. The movement of the internal panel allows cooled water to be communicated from the water reservoir 16 to the shroud 32. The internal panel may be placed on the water reservoir side of the partition (as shown in the attached figures), or it may be placed on the patient side of the partition. The shroud 32 will subsequently be deployed into position by the weight of the cooling solution which will exert pressure that preferably inflates the shroud 32 into close approximation to the patient's head, as described below.

In other presently preferred embodiments, the hammock is an entirely separate component from the watertight compartment. When the panel 24 is lowered in these embodiments, the hammock is, as with other embodiments, supported by the support cables 28. The hammock is in place to accept the patient's head before the watertight compartment that includes the shroud is deployed in these embodiments. In these embodiments, the hammock preferably includes fenestrations and is preferably connected to the wetting agent reservoir as described hereinbelow. In some of these presently preferred embodiments, the internal panel is located on the patient side of the wall of the water reservoir 16. In such embodiments, the internal panel holds the watertight compartment and shroud on the water reservoir side of the internal panel. When the panel is slid aside or removed, cooled water from the water reservoir fills the watertight compartment that includes a shroud and the hydrostatic pressure causes it to fill around the patient's head and the hammock. The final deployment of these embodiments is quite similar to that shown in FIGS. 2-6, but that the hammock and watertight compartment that includes a shroud are separate components here.

The placement of the shroud 32 may be maintained at the nose and neck of the patient by means of shroud straps 38.

Shroud straps 38 will ordinarily be fabricated either of loop-and-latch type materials such as those sold under the trademark VELCRO®, or will consist of adhesive tabs known in the art.

In certain preferred embodiments, the head hammock 36 and/or shroud 32 include fenestrations 40 as shown in FIG. 2 et seq. The fenestrations 40 are designed to irrigate the patient shroud interface and remove air and its insulating properties from cranial hair-bearing areas. The hammock 36 will preferably serve two roles—supporting the head and providing an internal irrigating system. The wetting system reservoir 42 is preferably connected to the hammock 36 via a connector tube 44. The connector tube 44 communicates wetting agent from the wetting reservoir 42 to a series of holes found in the shroud as seen in longitudinal view of FIG. 6. The wetting agent is any low viscosity, conductive fluid. One presently preferred wetting agent is water. The holes 48 are preferably located in the fenestrations 40 lining the hammock 36 indentation. The fenestrations 40 are adapted to allow passage of wetting agent to surround the patient's head effectively.

The apparatus of the present 10 may be utilized in the follow manner. If stored on a wall, the head cooling apparatus 10 may be initially removed from the wall and placed onto the ground such that the wheels or casters 22 contact the ground. The telescopic handle 20, if present, may be extended to allow easy transport of the apparatus to the patient in need of treatment.

Figure 3:
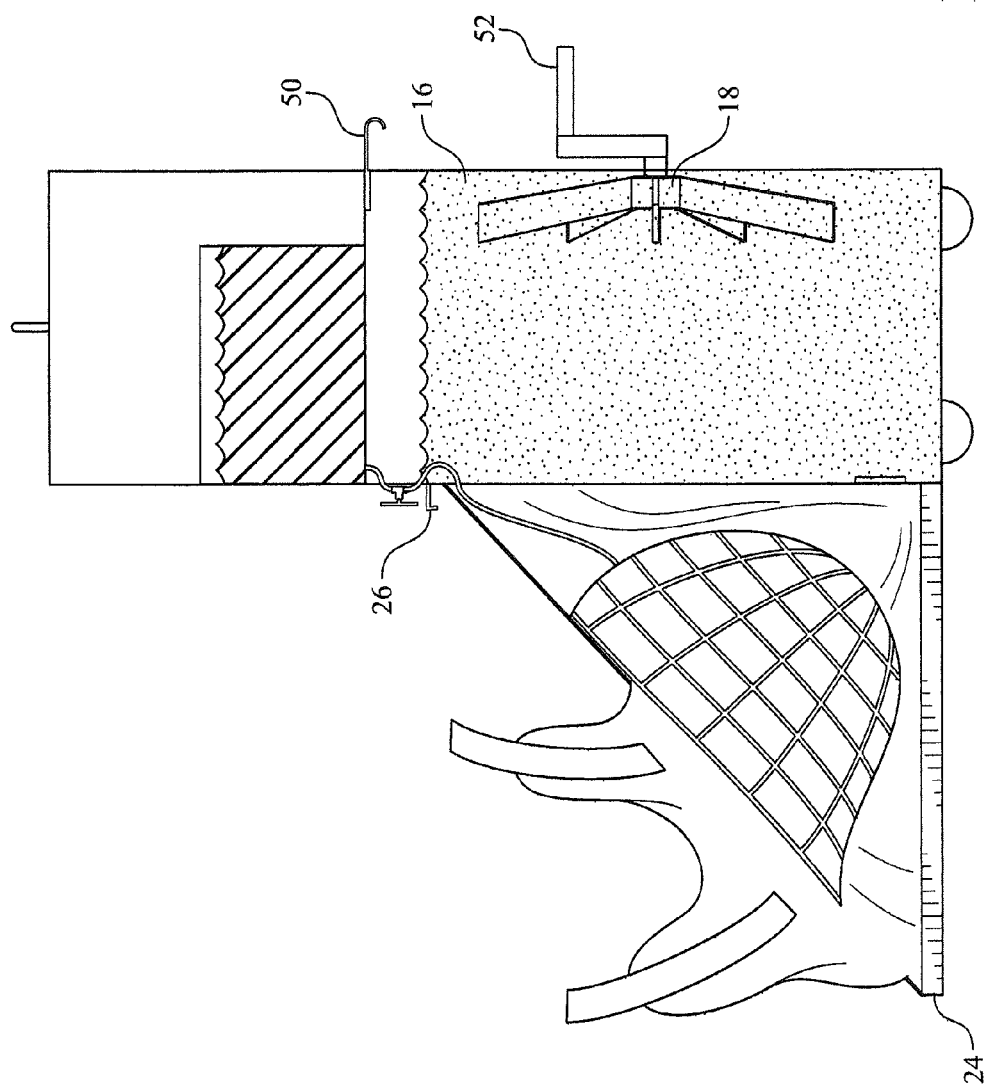
FIG. 3 is a cut-away view of a head cooling apparatus according to the present invention after the pellets have been drained into the water cooling chamber.

Once the head cooling apparatus 10 is near the patient, the latch 26 holding the panel 24 in the collapsed position may be opened and the panel 24 lowered in the deployed position as shown in FIG. 2. The user may then activate a latch 50 on the outside of the head cooling device 10 that allows the endothermic reaction pellets 14 to fall into the water reservoir 16, as shown in FIG. 3. In presently preferred embodiments, the endothermic reaction pellets 14 are ammonium nitrate. While the present application employs the term "pellets" as the form of endothermic reactant, it is to be understood that the ammonium nitrate may take the form of a combination of multiple pellet sizes or powder with pellets as described more fully hereinbelow. While the following description will employ the specific example of ammonium nitrate, other endothermic reactants are well known in the art and may be freely substituted for ammonium nitrate.

As the ammonium nitrate pellets 14 feed into the cooling water reservoir 16, the user may employ a rotatable mixer 18. In presently preferred embodiments, the rotatable mixer 18 is comprised of multiple spaced blades emanating radially from a center hub. The rotatable mixer 18 is preferably connected to an external crank handle 52. While the head cooling device is not deployed, the crank handle 52 may be folded into the body of the device to reduce it being an obstacle to nearby pedestrian traffic. When the device is deployed, the crank handle 52 may be folded out. The crank handle 52 will allow the ammonium nitrate pellets mix thoroughly, thus promoting dissolution and effective cooling.

Figure 4:
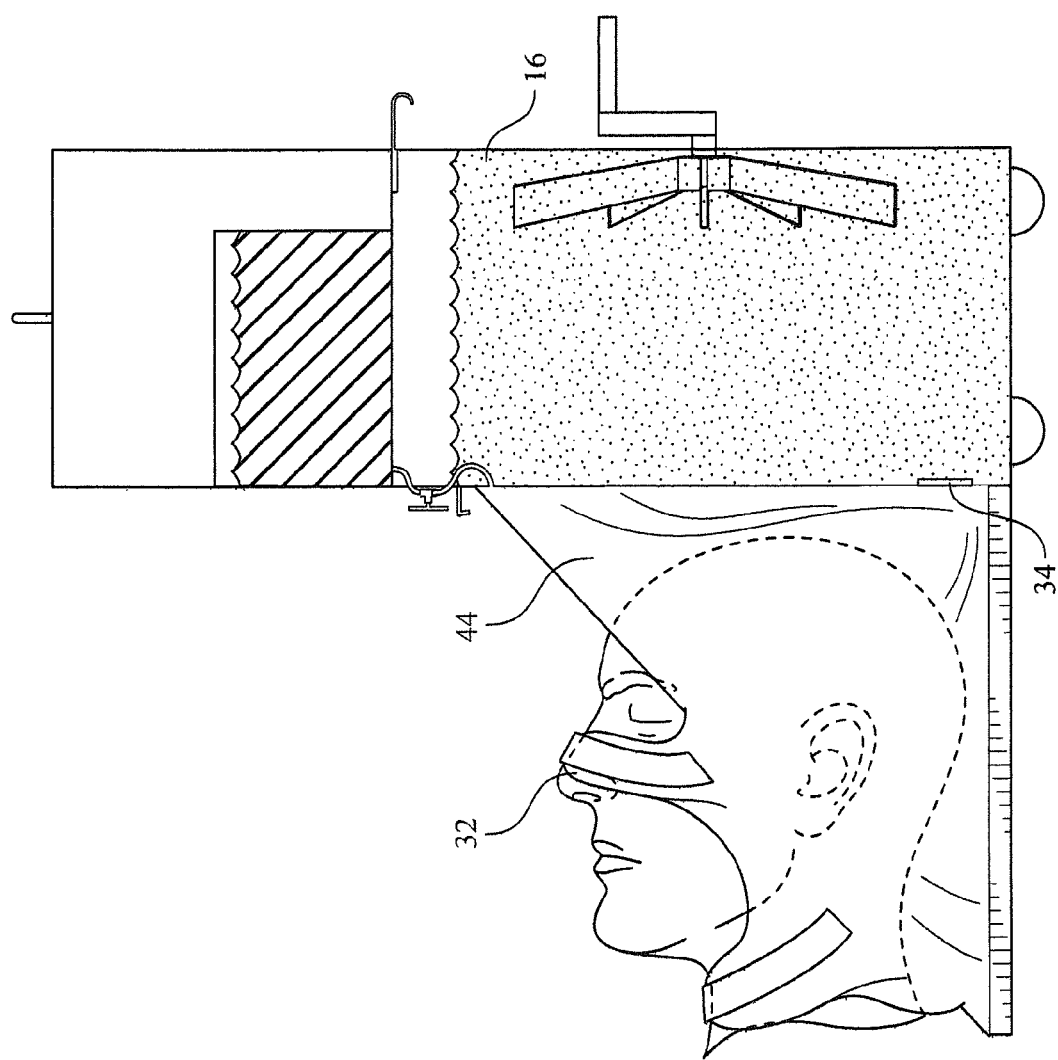
FIG. 4 is a cut-away view of a head cooling apparatus according to the present invention with a patient's head placed in the watertight head shroud.
Figure 5:
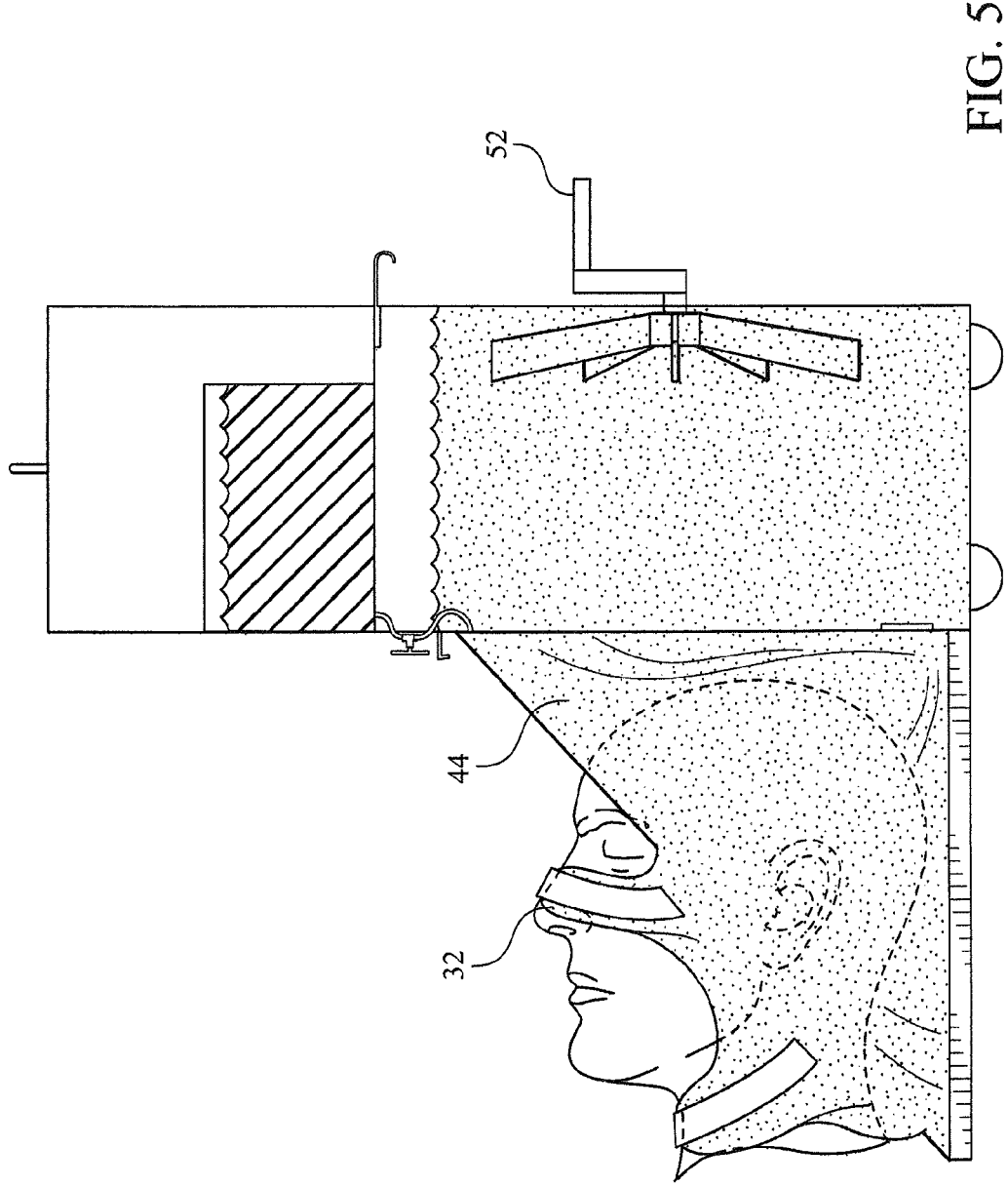
FIG. 5 is a cut-away view of a head cooling apparatus according to the present invention where the cooled water has been allowed to infiltrate the watertight head shroud.
Figure 6:
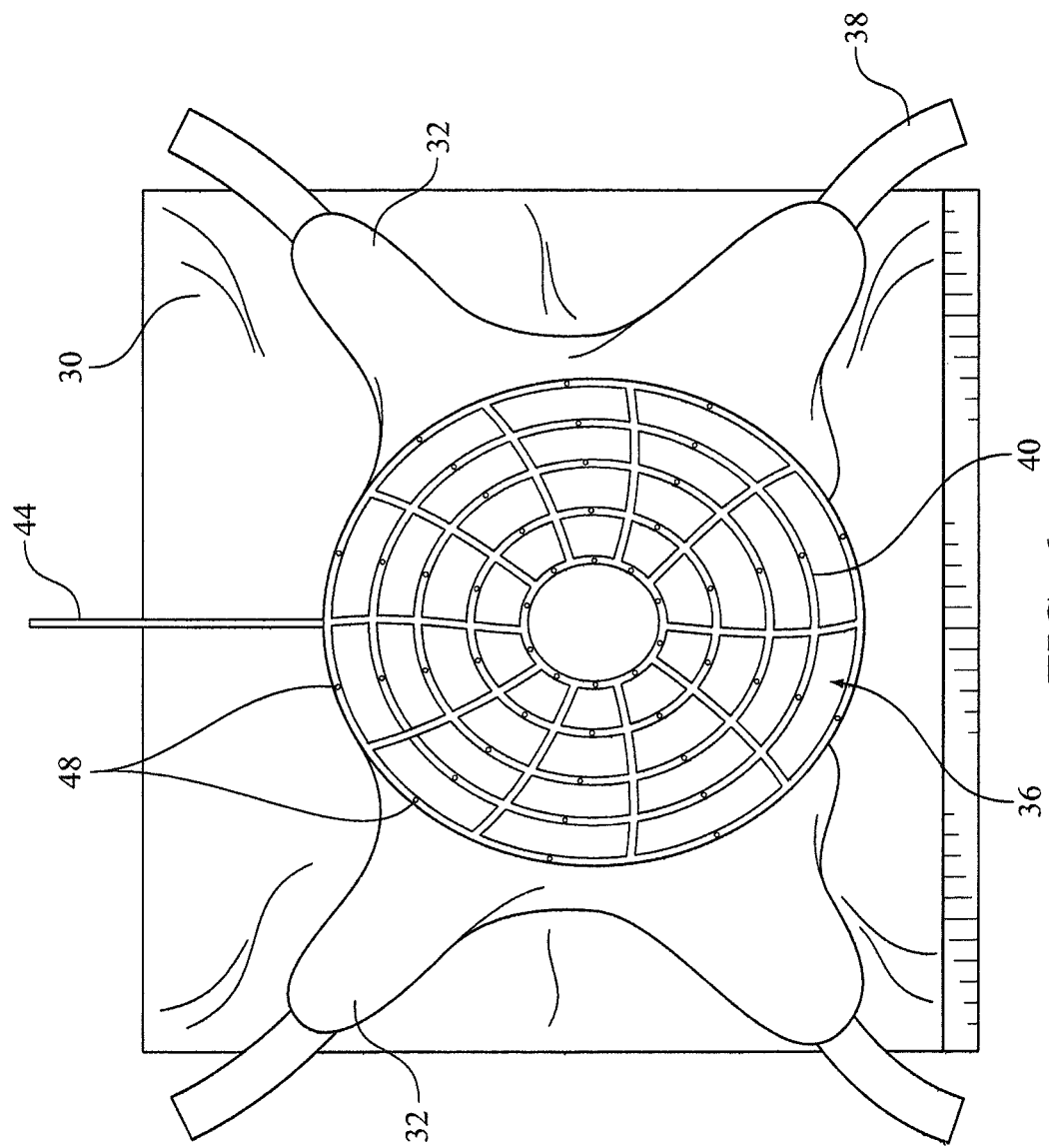
FIG. 6 is a longitudinal view of the hammock and shroud assembly of the present invention.

While the ammonium nitrate is dissolving into and cooling the water, the user of the head cooling device of the present invention 10 may place the patients head into the hammock 32 as shown in FIG. 4. After the patient's head has been placed in the hammock 32, the user may then activate an actuator located on the side of the device. When the actuator is activated, a panel 34 that lies between the water reservoir 16 and the watertight chamber is 44 altered to allow cooled fluid to drain into the watertight chamber 44, as shown in FIG. 5. The pressure caused by the influx of cooled water into the watertight chamber 44 preferably causes the shroud 32 to press firmly against the head of the patient, thereby promoting effective cooling of the cranial region of the patient. The shroud 32 may be secured to the patient's face through the use of the shroud straps 38.

It is commonly observed in the art that after some period of time the ammonium nitrate/water cooling system loses some of its effectiveness. It has been found that agitation of the system refreshes the reactants' efficacy. After the patient's head has been cooled for several minutes (e.g. approximately 15), the user may turn the crank handle 52 to reinvigorate the reaction conditions and maintain the reduced temperature in the cooling fluid. The rotational mixer 18 may also serve to freshen cooling gradients within the device. In prior art static head cooling systems, local warming of the cooling solution due to functional stasis would occur near the patient interface only being refreshed passively by convection and diffusion.

Certain presently preferred embodiments of the present invention may be adapted to be recharged with endothermic solids. In some presently preferred embodiments of the present invention, an access port (not shown) may preferably be located in the cooling chamber to allow addition of more endothermic solid, should such steps be needed during prolonged transport or treatment of the patient prior to the initiation of other cooling processes. The present invention may also include a deployable, detachable reservoir that includes fresh reactants. After the initially charged reactants are spent, they may be drained and the fresh reactants added from the reservoir. Alternatively, additional endothermic reactants may be added to the already charged solutions. In other present preferred embodiments, reservoirs containing additional endothermic reactant are included with the main structure of the present invention. The additional reactants may be discharged into the fluid reservoir surrounding the patient as needed to recharge the endothermic reaction periodically. Certain presently preferred embodiments of the present invention include a built-in reaction chamber thermometer which serves to guide the recharging process. In other preferred implementations of the present invention, the need for additional reactants may be assessed empirically by the user during application of the present invention to a patient.

The water in the water reservoir and the reactant in the endothermic reactant reservoir therefore can provide, when admixed, coolant fluid for which no external refrigeration is required. Water and ammonium nitrate are generally employed in equal parts by weight, or at a ratio of about 1:1 by weight, and further are ordinarily incorporated into the system in the amount of 4-5 kg. each. With the combined weight of the reactants being approximately 8-10 kg., the entire system routinely weighs approximately 11-12 kg., or 25 lbs.

Prior art head cooling devices employ a single population of ammonium nitrate pellets to participate in the endothermic reaction. The present invention provides an improved distribution of reactant pellets that provides for a customization of the cooling curve generated by the endothermic reaction. The prior art generally desired a cooling curve that did not descend below freezing, so as to avoid potential frostbite-inducing conditions, but rather achieve a constant degree of cooling. This approach, however, did not result in cooling deep brain regions, which would require a more significantly reduced surface temperature.

In contrast, the present invention specifically provides a distribution of solid ammonium nitrate that produces a "burst" of transient initial cooling that may briefly enter into subfreezing temperatures. Once the system reaches thermodynamic equilibration, the temperature will return to depressed, but above-freezing temperatures. That temperature profile more rapidly initiates therapeutic hypothermia through steeper cooling gradients than those provided in the prior art.

To investigate the thermochemical basis for the present invention, a series of calometric experiments were run. Reactant water (120 milliliters) was placed in a metal container and the container was in turn placed into a water bath. Various forms of reactants were added and the temperature of the interface between the bath and the metal container was measured. Throughout all of the experiments described below, while the reactants themselves were often below freezing, the exterior surface of the metal container did not display frost and did not produce sub-freezing temperatures. Interface temperature rather than water bath temperature was measured to document that the patient would not be exposed to sub-freezing reactant temperatures. While the water bath was not necessarily representative of the physiological patient, it nonetheless allowed the comparison of the prior art distributions of ammonium nitrate with the distributions employed by the present invention.

Figure 7:
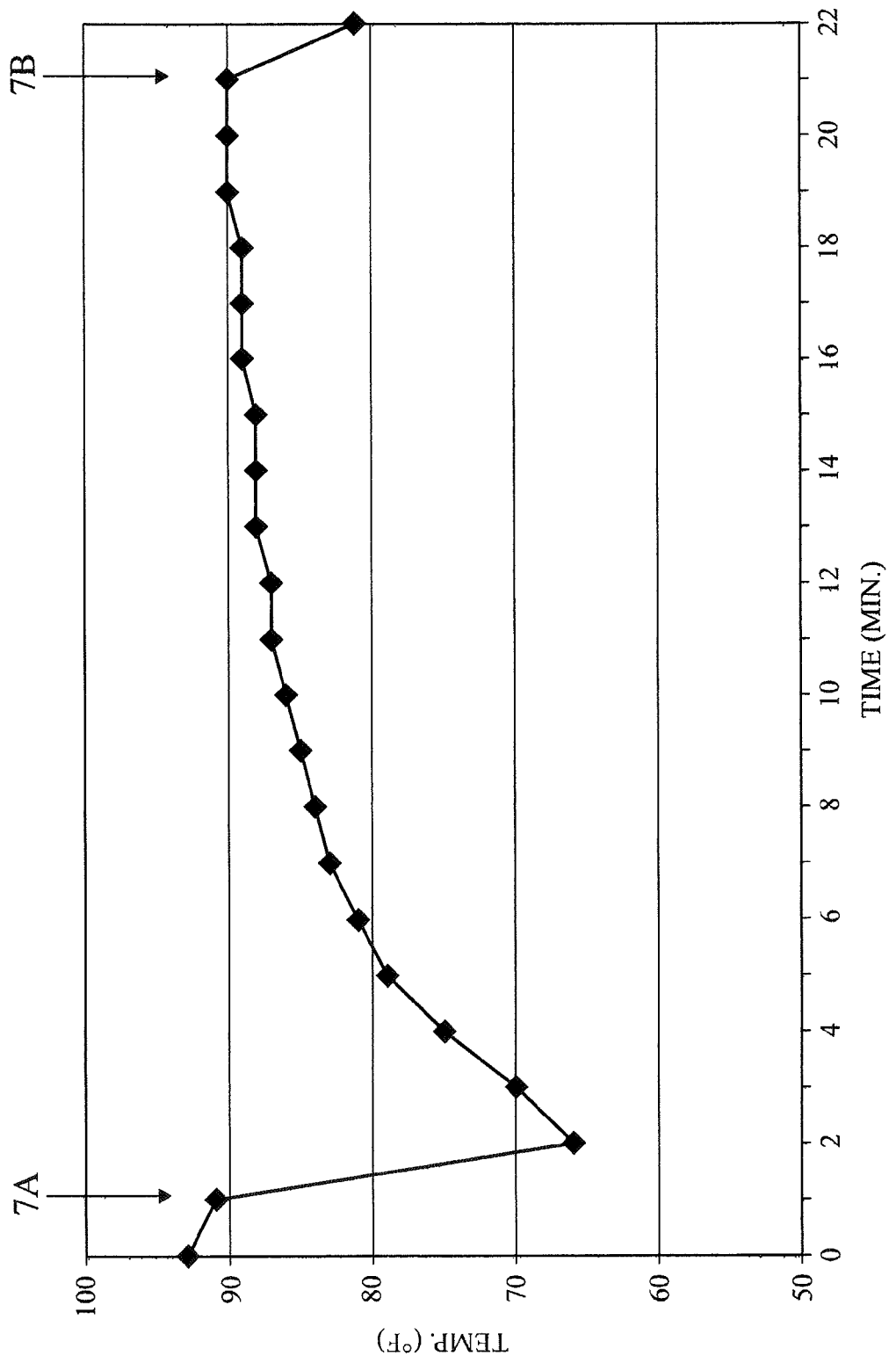
FIG. 7 is a cooling curve from calometric experiments employing a distribution of ammonium nitrate pellets from the prior art.

In the experiment shown in FIG. 7, a relatively large volume water bath was initially held at approximately 93° F. At the time indicated by arrow 7A, a single packet of commercially available pellets of ammonium nitrate (55 mg) were added to the reactant water (120 milliliters). The pellets have a uniform distribution of pellets with a diameter of approximately 3 mm. As can be seen in FIG. 7, the temperature of the interface dropped precipitously upon addition of the reactant pellets and subsequently relaxed towards the initial temperature. At the time indicated by arrow 7B, the reactants were stirred. The undissolved pellets, thus, were reactivated thereby reducing water temperature again. This observation further indicates that stirring reactants in the head cooling devices of the present invention would be beneficial to the efficient cooling of the patient's head.

Figure 8:
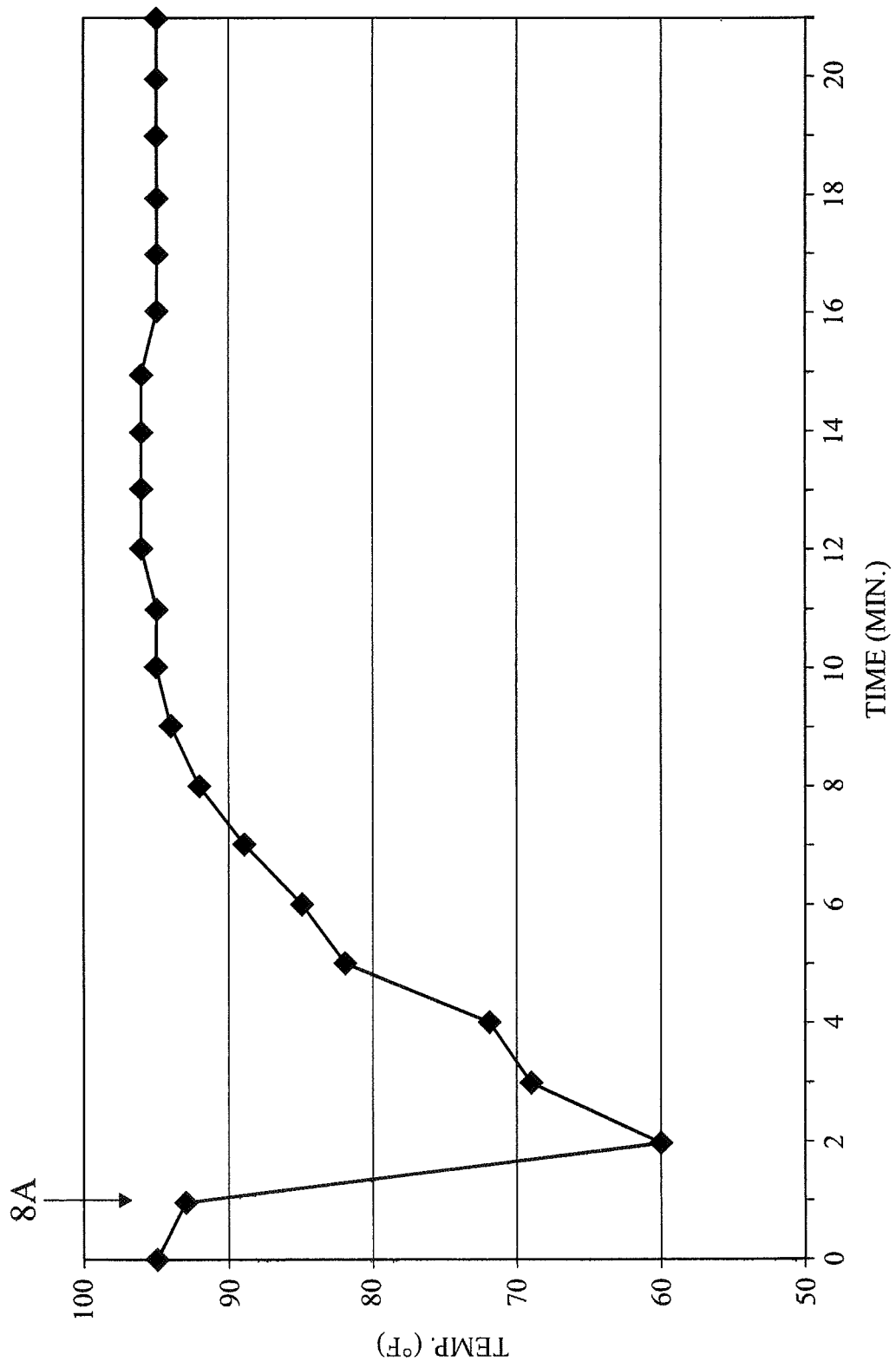
FIG. 8 is a cooling curve from calometric experiments employing a distribution of ammonium nitrate pellets from the prior art with repeated stirring.

A follow-up experiment was performed (FIG. 8) to assess the impact of consistent stirring on the ability of ammonium nitrate pellets to lower the reactant water, and thus the interface, temperature. In this experiment, a single packet of prior art ammonium nitrate pellets was added to the reactant water at arrow 8A. Unlike the experiment shown in FIG. 7, the reactant mixture was stirred for 30 seconds every two minutes. As may be seen, the reactant water reached a much lower temperature than without stirring (cf. the nadirs in FIGS. 7 and 8) indicating that stirring has a significant impact on the operation of cooling systems.

Figure 9:
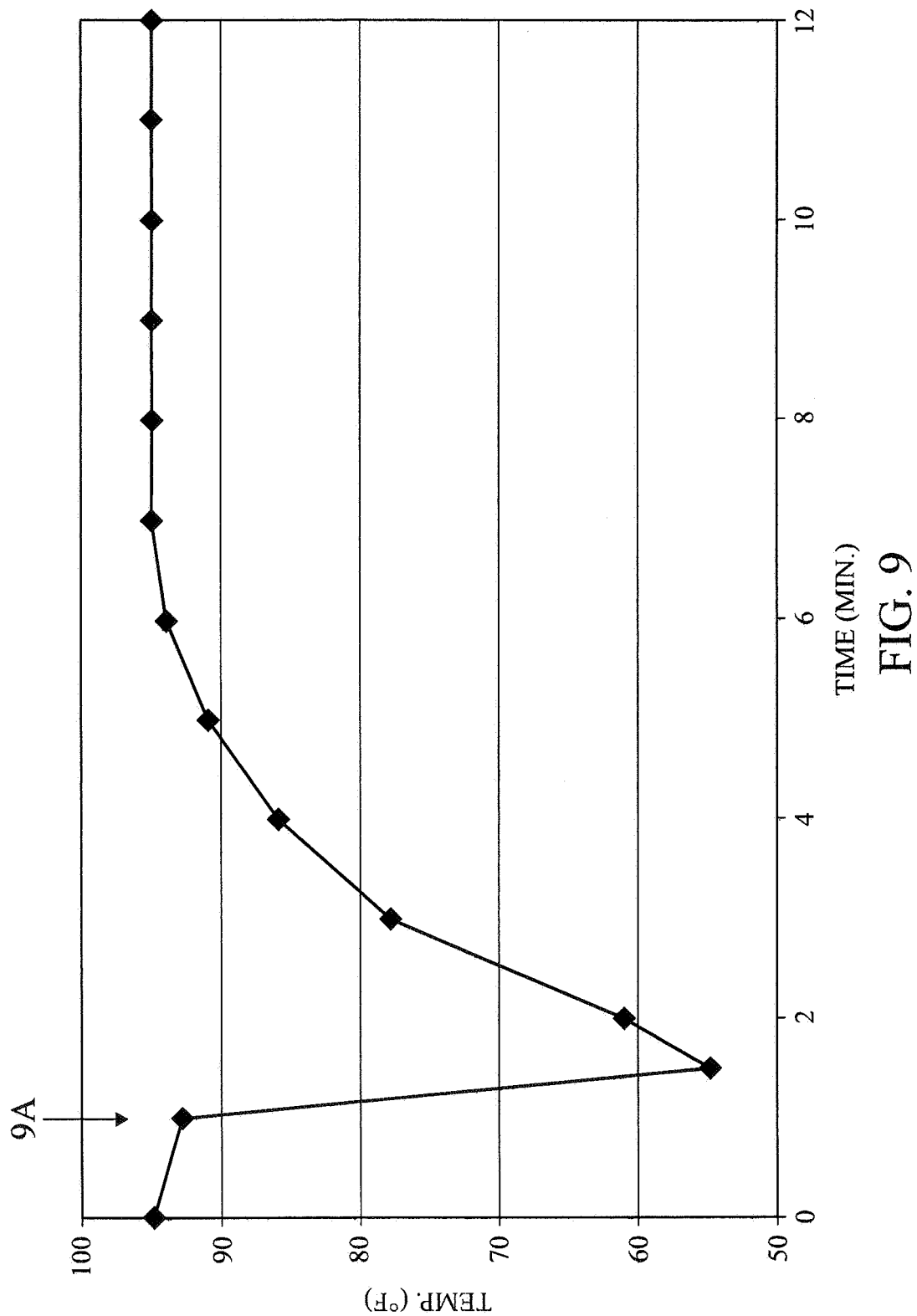
FIG. 9 is a cooling curve from calometric experiments employing powdered ammonium nitrate.

In the experiment whose results are reported FIG. 9, a single packet of prior art ammonium nitrate pellets was crushed into fine powder and was subsequently added to the reactant water at arrow 9A. The reactant mixture was continuously stirred. As can be clearly seen, the reactant mixture quickly reached a very low temperature and, in addition, rapidly returned to initial temperatures—thus indicating that the ammonium nitrate rapidly dissolves and is rapidly spent in the reaction mixture. While such a distribution of ammonium nitrate would result in rapid and extreme cooling of cranial and peri-cranial tissue in the context of the present invention, it would lack the long-term reduction of surface temperature that is desired for the present invention.

Figure 10:
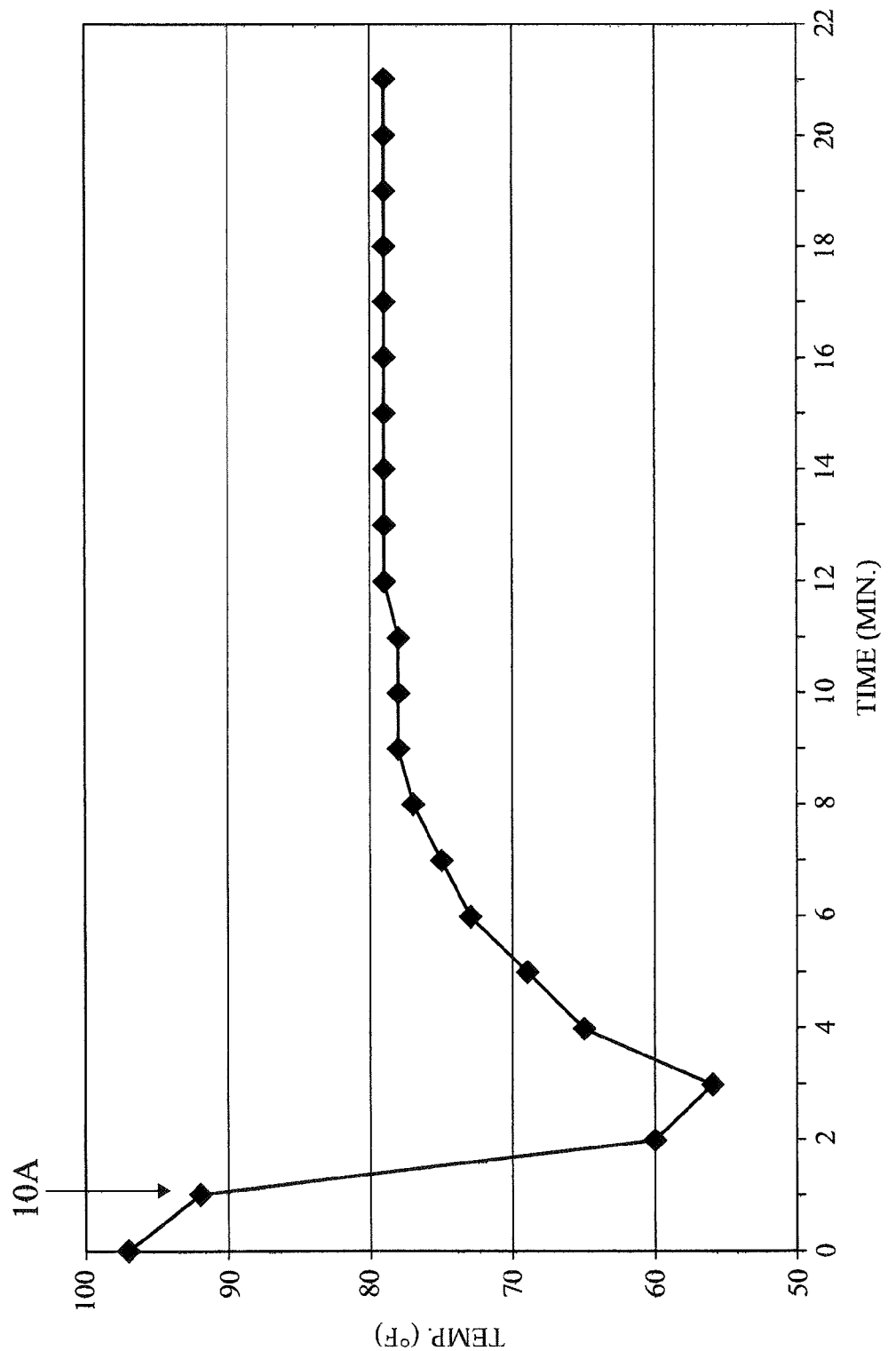
FIG. 10 is a cooling curve from calometric experiments employing larger volumes of powdered ammonium nitrate.

To assess the limits of the powdered ammonium nitrate in reducing temperature, a further experiment was performed FIG. 10. These experiments employed a water bath of reduced mass/volume in proportion to the anticipated patient head size relative to the mass of reactants used, thus simulating the clinical situation and estimating relative equilibrium points. Specifically, three packs (165 mg) of ammonium nitrate were added to 360 milliliters of reactant water at the time indicated by arrow 10A. The reactants were continuously stirred. Again, the temperature in the water bath rapidly fell and returned to a reduced temperature (~80° F.). This result indicates that the reaction mixture was not saturated typical cold pack ratio of reactants of ammonium nitrate and that additional ammonium nitrate could be added to the system for prolonged cooling.

Figure 11:
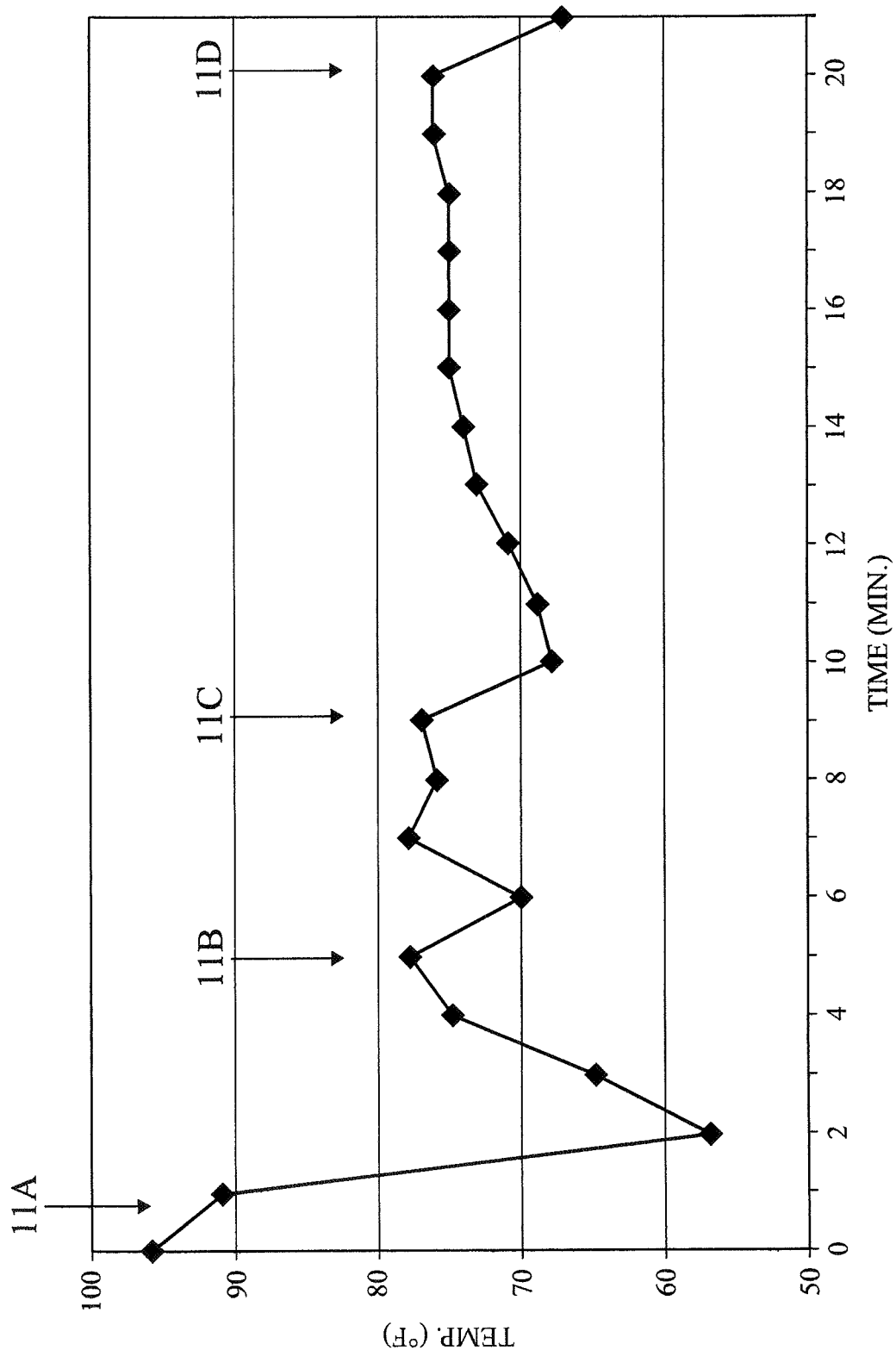
FIG. 11 is a cooling curve from calometric experiments employing a combination of powdered ammonium nitrate and pelleted ammonium nitrate.

On the basis of the above-described experiments, an additional experiment was performed as shown in FIG. 11. The experiment was designed to assess whether intermittent addition of ammonium nitrate pellets to a reaction mixture could result in improved sustained cooling. At the time indicated by arrow 11A, two packets of powdered ammonium nitrate were added to the reactant water and the reactants were continuously stirred. As expected from the results described above, the reactant temperature dropped quickly. As the reactant mixture warmed, a third packet of ammonium nitrate pellets were added at the time indicated by arrow 11B. The temperature quickly dropped. Subsequent addition of ammonium nitrate at the times indicated by arrows 11C and 11D demonstrated that the reactant mixture was not saturated with ammonium nitrate and that large volumes of ammonium nitrate can effectively cool a reaction mixture.

The present invention extrapolates from these sets of experiments to propose a novel distribution of solid endothermic reactants to be utilized in the head cooling systems of the present invention. The present invention accomplishes the improved cooling profile through the use of a novel distribution of solid endothermic reactant. The present invention includes a distribution of solid endothermic reactant having a diversity of sizes. In some presently preferred embodiments, the distribution includes pellets having two or more diameters. Preferably, at least a portion of the population of pellets is of very small diameter, from approximately 2 millimeters to a finely ground powder. Larger pellets having an approximate diameter of about 5 to about 10 millimeters or more depending on the desired effect are also preferably included in the mixture for the maintenance of mild hypothermia after return of circulation in the patient or as part of the second phase of intra-arrest cooling/recharging. In presently preferred embodiments, the preferred diameter of the large diameter pellets is 7 millimeters. The larger pellets would sustain cooling over a longer period of time. Once the endothermic reaction is initiated, the small diameter pellets react very rapidly with the water as indicated by the above-described experiments, thereby effecting a quick and strong reduction in the temperature of the solution. The duration of the rapid and strong temperature reduction may be adjusted by the amount of very small diameter pellets that are included. As the reaction of the very small diameter pellets is exhausted, the temperature will typically relax to slightly warmer temperatures, though the continued reaction of the larger pellets preferably maintains the temperature at a level sufficient to induce hypothermia. By including multiple distributions of pellets in the invention, a customized cooling curve may be generated according to the specific applications that are intended for the cooling solution. In addition to coolants of varying size, the present invention contemplates inclusion of a retardant with some populations of solid endothermic reactant to achieve a similar effect as a varied distribution of pellet size. The retardant would act to slow the dissolution of the endothermic reactant and thus influence the cooling of the reaction mixture.

Figure 12:
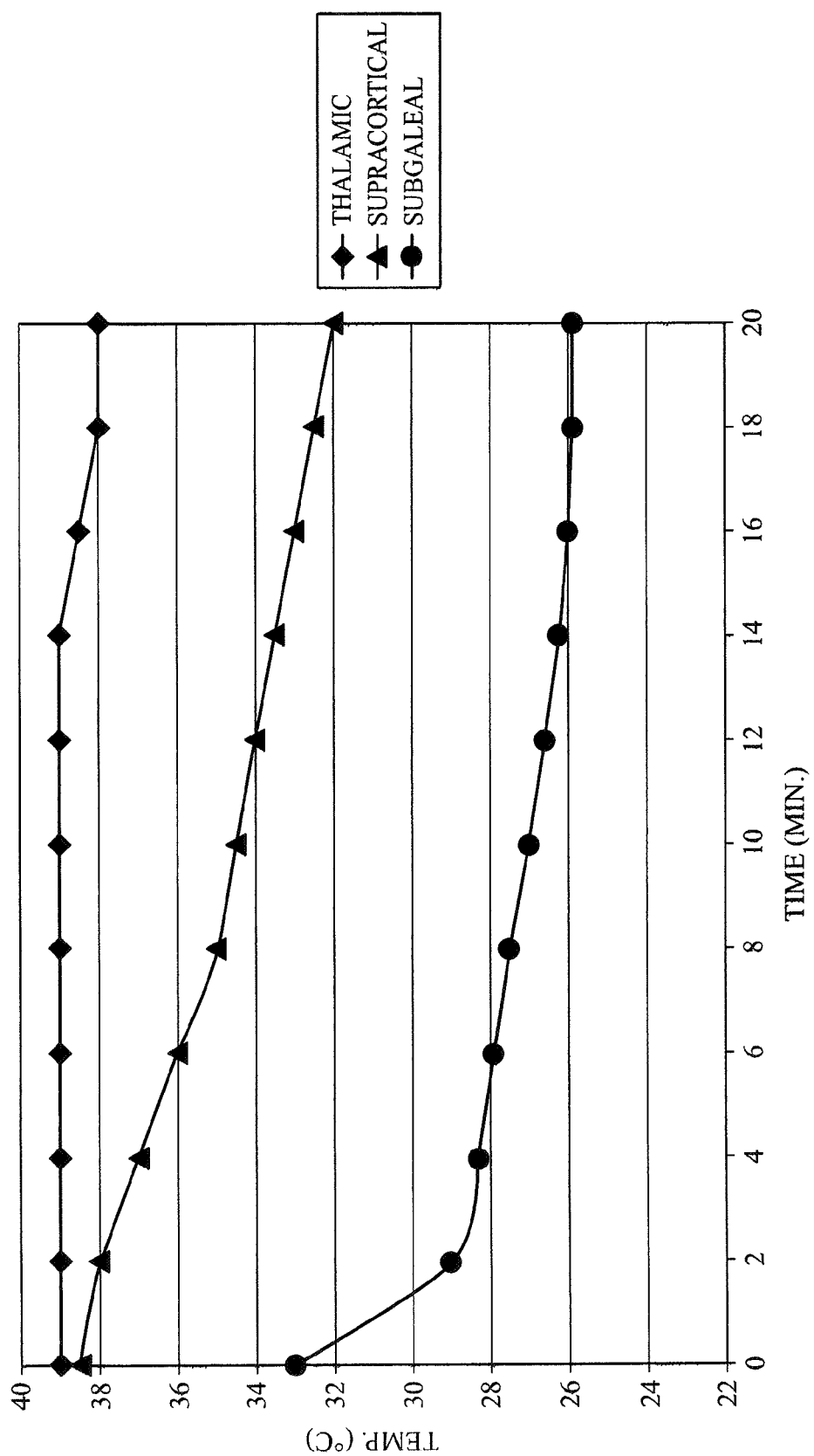
FIG. 12 is physiological temperature data recordings from an animal model employing a prior art head cooling device.
Figure 13:
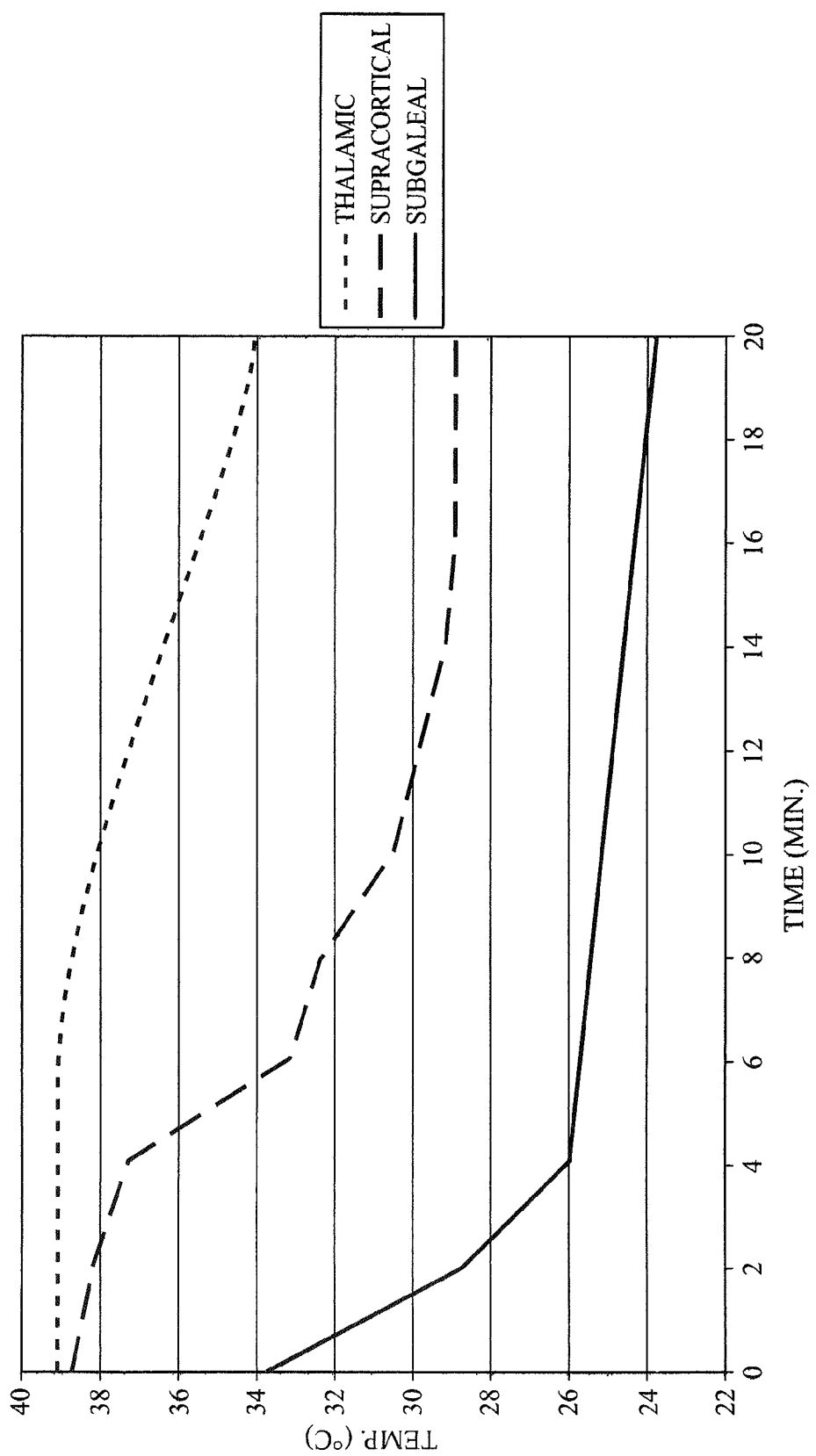
FIG. 13 displays an improved cooling curve of the present invention.

The effects observed using mixtures of endothermic reactant having variable distribution compared to the prior art may be seen in FIGS. 12 and 13. FIG. 12 displays data collected from an animal model using a prior art head cooling device.

Specifically, a 25 kg canine with similar extracranial soft tissue depth and bony thickness to adult human was employed. External hair was shaved with clippers. Temperature thermistors were surgically tunneled posteriorly between the soft tissue and the skull beginning in the neck so that transmission cables had no direct contact with cooling solution interface. Intracranial thermistors were inserted through small burr holes in the skull, epidural and thalamic, to minimize conduction through the skull defect in addition to extensive tunneling. Cardiac arrest was induced electrically, the animal's head was moistened, and the head cooling device applied using a single distribution of solid 4 mm ammonium nitrate pellets. Temperature was recorded in deep brain structures (thalamus), superficially in the brain (supracortical), and in a subgaleal structure (underneath the scalp muscle layer). Temperatures were recorded continuously. The reactants were subjected to intermittent stirring. As can be seen in FIG. 12, the temperature of the superficial tissues was reduced, though deep brain structures, such as the thalamus were relatively unaffected.

In contrast, a head cooling device of the present invention as employed with a multi-component distribution of solid ammonium nitrate could be expected to produce cooling curves as displayed in FIG. 13. The decreased temperature at the surface of the skin afforded by the present invention would result not only in cooling of the superficial structures, but also of deep brain structures, thus providing increased protection from hypoxic/ischemic-triggered cell death. This aspect of the present invention relating to nonlinear cooling curve production is also applicable to other external cooling systems, such as systems that use either reactants other than ammonium nitrate or systems that employ other mechanical cooling procedures.

Nothing in the above description is meant to limit the present invention to any specific materials, geometry, or orientation of elements. Many part/orientation substitutions are contemplated within the scope of the present invention and will be apparent to those skilled in the art. The embodiments described herein were presented by way of example only and should not be used to limit the scope of the invention.

The invention claimed is:

1. An apparatus for the rapid cooling of a cranial region of a patient, comprising:
   an external housing that houses:
      a watertight compartment adapted to form a shroud that extends over the forehead, face, neck, and a top, back, and sides of said patient's head;
      an endothermic reactant reservoir containing a quantity of solid endothermic reactant which reacts endothermically with water;
      a water reservoir containing water, comprising a structural tank that includes a first movable internal panel that separates said structural tank and said endothermic reactant reservoir and a second movable internal panel that blocks said watertight compartment from filling with water, wherein said apparatus may be stored in a collapsed state; and
      a hammock adapted to accept the patient's head, wherein said hammock is adapted to fit within said shroud; and
   a front panel attached at its proximal base to the base of said external housing by a hinge, wherein said front panel is attached at its distal base to the external housing by two support bands extending from the distal base of said front panel to said external housing at a distance above the base of the external housing, wherein said hammock is supported by said support bands, further wherein said watertight compartment is located behind said front panel when said front panel is in a closed configuration.

2. The apparatus of claim 1, further comprising a mechanism for attaching said shroud to the patient's head.

3. The apparatus of claim 1, further comprising a wetting agent reservoir, wherein said wetting agent reservoir is functionally connected to said hammock through a connector tube that terminates in a series of holes in said hammock.

4. The apparatus of claim 3, wherein said hammock includes fenestrations that form channels around an interior of said hammock.

5. The apparatus of claim 4, wherein said series of holes is located in said fenestration.

6. The apparatus of claim 1, wherein said watertight compartment is supported by an insulated panel below said watertight compartment.

7. The apparatus of claim 1, wherein said solid endothermic reactant is ammonium nitrate.

8. The apparatus of claim 1, wherein said solid endothermic reactant is present as a distribution of solids.

9. The apparatus of claim 8, wherein said distribution of solids includes large diameter pellets and small diameter particles.

10. The apparatus of claim 9, wherein said large diameter pellets have a diameter between about 5 millimeters to about 10 millimeters.

11. The apparatus of claim 10, wherein said large diameter pellets have a diameter of about 7 millimeters.

12. The apparatus of claim 9, wherein said small diameter particles are powder.

13. The apparatus of claim 9, wherein said small diameter particles have a diameter of about 2 millimeters.

14. The apparatus of claim 1, wherein said first movable internal panel is adapted to be moved to allow movement of said solid endothermic reactant from said endothermic reactant reservoir to said water reservoir.

15. The apparatus of claim 1, wherein said second movable internal panel is adapted to be moved to allow movement of water from said water reservoir into said watertight compartment.

16. The apparatus of claim 1, further comprising a telescopic handle connected to said external housing.

17. The apparatus of claim 1, further comprising wheels or casters of the bottom of said external housing.

18. A method for cooling a head of a patient in need thereof, comprising the steps of:
   obtaining a collapsed head cooling device, wherein said head cooling device comprises:
      an external housing that houses:
         a watertight compartment adapted to form a shroud that extends over the forehead, face, neck, and a top, back, and sides of said patient's head;
         an endothermic reactant reservoir containing a quantity of solid endothermic reactant which reacts endothermically with water; and
         a water reservoir containing water, comprising a structural tank that includes a first movable internal panel that separates said structural tank and said endothermic reactant reservoir and a second movable internal panel that blocks said watertight compartment from filling with water, wherein said apparatus may be stored in a collapsed state;
   lowering a front panel to open said collapsed head cooling device, wherein said front panel is attached at its proximal base to the base of said external housing by a hinge, wherein said front panel is attached at its distal base to the external housing by two support bands extending from the distal base of said front panel to said external housing at a distance above the base of the external housing, further wherein said support bands support a hammock;

opening said first movable internal panel, thereby allowing said solid endothermic reactant to enter said water reservoir;

allowing said solid endothermic reactant and said water to react, thereby cooling said water;

placing said head of said patient into said hammock;

opening said second movable internal panel, thereby allowing said water to fill said watertight compartment; and closing said shroud over said patient's head.

19. The method of claim 18, wherein said solid endothermic reactant is present as a distribution of solids.

20. The method of claim 19, wherein said distribution of solids includes large diameter pellets and small diameter particles.

21. The method of claim 20, wherein said large diameter pellets have a diameter between about 5 millimeters to about 10 millimeters.

22. The method of claim 21, wherein said small diameter particles are powder.

23. The method of claim 21, wherein said small diameter particles have a diameter of about 2 millimeters.

24. The method of claim 21, wherein said large diameter pellets have a diameter of about 7 millimeters.

* * * * *